United States Patent
Sawers

(10) Patent No.: US 9,789,330 B1
(45) Date of Patent: Oct. 17, 2017

(54) APPARATUS FOR TRANSCRANIAL MAGNETIC STIMULATION

(71) Applicant: Knowledge Technologies, LLC, Charleston, SC (US)

(72) Inventor: James R. Sawers, Charleston, SC (US)

(73) Assignee: Knowledge Technologies, LLC, Charleston, SC (US)

( * ) Notice: Subject to any disclaimer, the term of this patent is extended or adjusted under 35 U.S.C. 154(b) by 247 days.

(21) Appl. No.: 14/922,951

(22) Filed: Oct. 26, 2015

Related U.S. Application Data

(60) Provisional application No. 62/069,678, filed on Oct. 28, 2014.

(51) Int. Cl.
| | |
|---|---|
| A61N 1/00 | (2006.01) |
| A61N 2/00 | (2006.01) |
| A61N 2/02 | (2006.01) |
| A61M 37/00 | (2006.01) |

(52) U.S. Cl.
CPC ............. *A61N 2/006* (2013.01); *A61N 2/002* (2013.01); *A61N 2/02* (2013.01); *A61M 2037/0007* (2013.01)

(58) Field of Classification Search
CPC .......... A61N 2/00; A61N 2/002; A61N 2/004; A61N 2/006
USPC ........................................................ 600/9–15
See application file for complete search history.

(56) References Cited

U.S. PATENT DOCUMENTS

| | | | |
|---|---|---|---|
| 6,066,084 A | 5/2000 | Edrich et al. | |
| 7,771,341 B2 | 8/2010 | Rogers | |
| 8,657,731 B2 | 2/2014 | Riehl et al. | |
| 2005/0256539 A1 | 11/2005 | George et al. | |
| 2006/0199992 A1 | 9/2006 | Eisenberg et al. | |

FOREIGN PATENT DOCUMENTS

| | | |
|---|---|---|
| CN | 1224367 A | 7/1999 |
| CN | 1224367 C | 10/2005 |
| EP | 1273320 A1 | 1/2003 |
| EP | 1273320 B1 | 4/2005 |
| JP | 11513907 A5 | 11/1999 |
| JP | 2007160078 A | 6/2007 |

(Continued)

OTHER PUBLICATIONS

Yiftach Roth, Alon Amir, Yechiel Levkovitz, and Abraham Zangren; Article entitled: Three-Dimensional Distribution of the Electric Field Induced in the Brain by Transcranial Magnetic Stimulation Using Figure-8 and Deep H-Coils; Journal of Clinical Neurophysiology, p. 31-38; Feb. 2007.

(Continued)

*Primary Examiner* — John Lacyk
(74) *Attorney, Agent, or Firm* — Nexsen Pruet, LLC; Michael A. Mann

(57) ABSTRACT

A quadrupolar-solenoidal electro-magnet creates more nearly parallel field lines and a coaxial magnetic bias resulting in allowing deeper magnetic field penetration with reduced depth attenuation and greater focality than available with the commonly used Figure-8 dual toroidal magnets, thereby overcoming the trade-offs inherent in currently standard practice for transcranial magnetic stimulation magnetic field generation and the proposed transcranial magnetic stimulation coil designs. When quadrupole electro-magnets are used with solenoids, the axis of the electro-magnets can be focused at the target within the desired tissue and at greater depth.

20 Claims, 5 Drawing Sheets

(56) References Cited

FOREIGN PATENT DOCUMENTS

| JP | 4545722 B2 | 9/2010 |
|---|---|---|
| JP | 11513907 A | 8/2013 |
| KR | 1020000022564 A | 4/2000 |
| WO | WO9700639 | 1/1997 |
| WO | WO-9740887 A1 | 11/1997 |
| WO | WO-02089902 A2 | 11/2002 |
| WO | WO-02089902 A3 | 11/2002 |
| WO | WO-2004100765 A2 | 11/2004 |
| WO | WO-2004100765 A3 | 11/2004 |

OTHER PUBLICATIONS

Zhi-De Deng, Angel V. Peterchev, Sarah H. Lisanby; article entitled: Coil Design Considerations for Deep-Brain Transcranial Magnetic Stimulation (dTMS); from 30th Annual IEEE EMBS Conference, Vancouver, British Columbia, Canada ; Aug. 20-24, 2008 Aug. 20, 2008.

Zhi-De Deng, Angel V. Peterchev, Sarah H. Lisanby; Article entitled: Electric Field Depth-Focality Tradeoff in Transcranial Magnetic Stimulation: Stimulation Comparison of 50 Coil Designs; from Brain Stimulation Jun. 1-13, 2013; Apr. 4, 2012 Apr. 4, 2012.

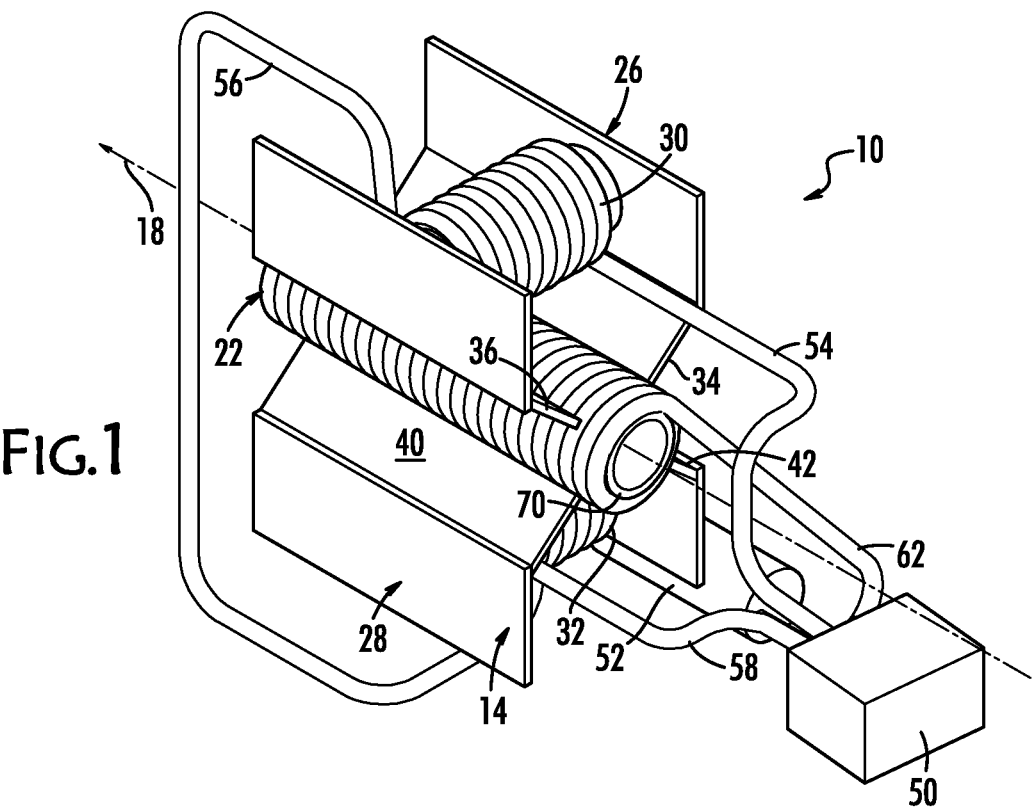
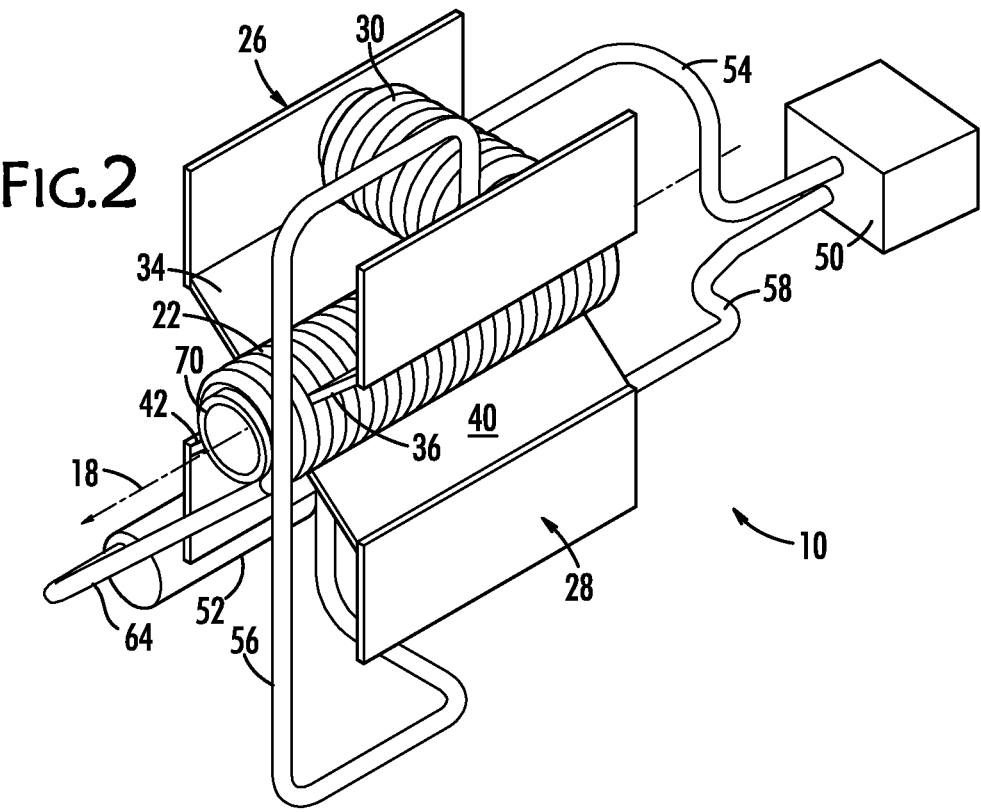

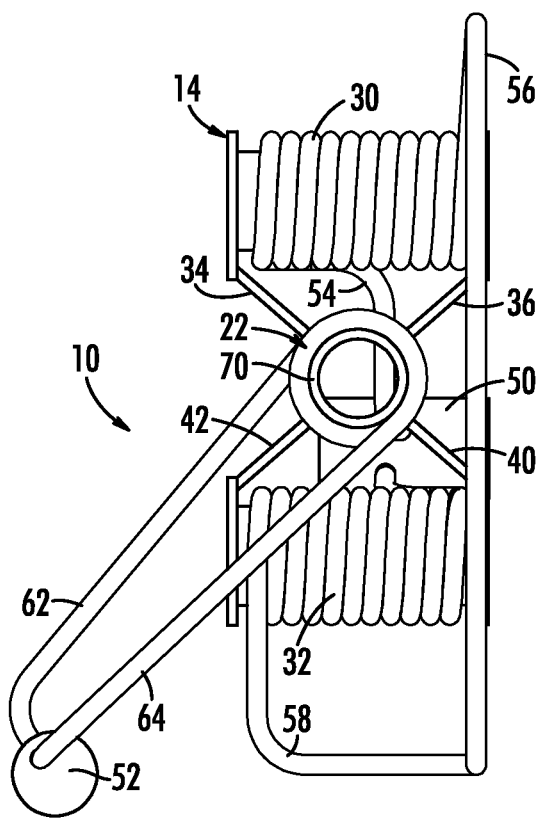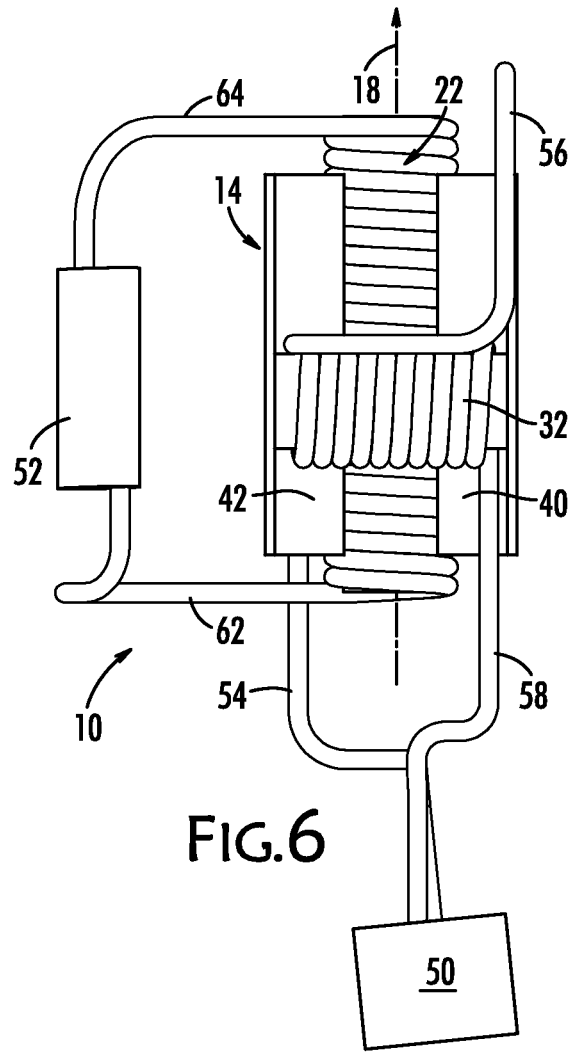

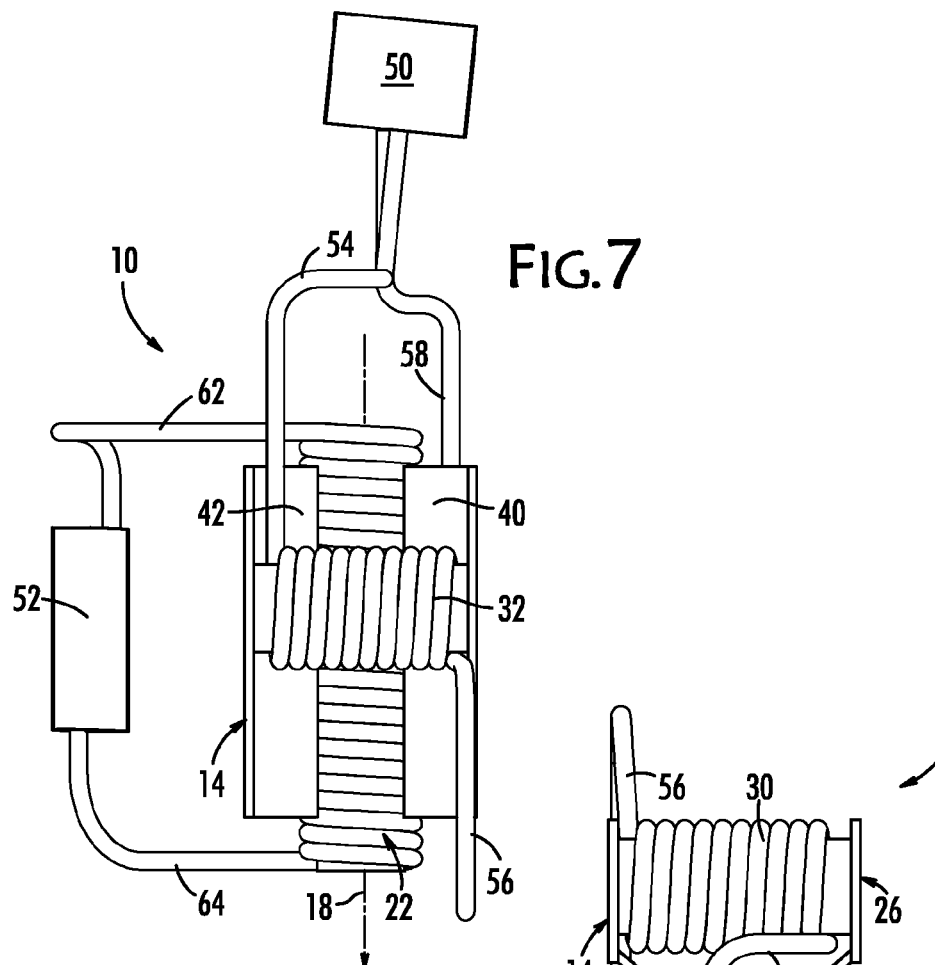
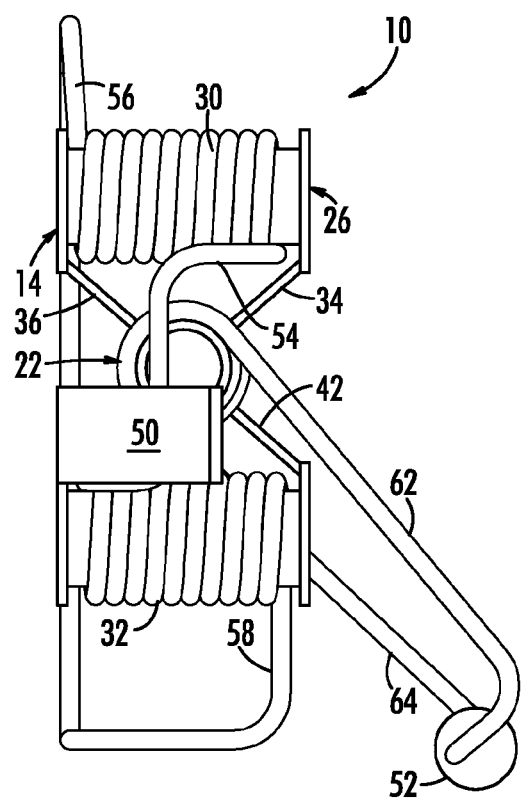

APPARATUS FOR TRANSCRANIAL MAGNETIC STIMULATION

BACKGROUND

Transcranial magnetic stimulation (TMS) is a non-invasive technique that is used clinically and as an investigatory method in many research and therapeutic applications. Use of TMS on both normal and pathological brain functions has been studied, and TMS has been used in the treatment of neurological and psychiatric disorders including major depression, schizophrenia, dystonia, autism, pain relief, and chronic migraine. Magnetic fields can penetrate and induce electric fields in tissue of other types, as well, tissues such as muscle, liver, and kidney.

Traditionally, TMS uses brief, intense pulses of electric current delivered to a coil placed adjacent to the subject's head. During the pulses, changes in the magnetic field internal to the target brain tissue create resultant electric fields within the brain via electro-magnetic induction. The induced electric field modulates the neural transmembrane potentials and, hence, neural activity. The focus of activation in the brain is approximated by the volume where the induced electric field is nearly maximal. This location depends on stimulating coil field strength, coil geometry, and coil placement.

A dual toroid Figure-8 magnet configuration is commonly used for generating the magnetic field for brain stimulation, but a variety of innovative coil designs are now being proposed and studied.

To map direct neural activity stimulated using TMS, the induced electric field distributions generated by different coil designs have been characterized by theoretical calculations, numerical simulation models, and measurements of the electric currents induced in phantoms or in vivo. Analytical studies have used idealized circular and Figure-8 coil geometries. Only a few commercial coils have been modeled in computational analyses. Thus, field distribution data for many commercial, experimental, or proposed TMS coil designs remain unavailable. Knowledge of electric field spatial distributions generated with specific coil designs and how these fields compare with those generated by alternative coil designs is valuable in the design and interpretation of basic research and clinical studies. Indubitably, the development of novel coil design has been inhibited by the lack of theoretical comparison of the efficacy of presently available or proposed designs.

The two most salient electric field spatial considerations with respect to TMS are depth of penetration (especially field attenuation with depth and with respect to orientation of the coil's major axis) and focality—the ability of a chosen coil to focus (concentrate) a magnetic field deep within the subject tissue. Actual proposed or implemented coil designs have been developed with the objective of improving one or both of these field characteristics. All designs require a tradeoff between attenuation with depth and focality. Focality is important in attempting to target small volumes while simultaneously avoiding similar effects in adjacent non-targeted volumes.

There has also been substantial interest in direct, non-invasive stimulation of brain volumes deeper than the superficial cortex, but electric fields in such deep brain targeting capability is limited by the rapid attenuation with penetration depth. Fields from larger coils penetrate deeper but have reduced focality. Reduced focality is a serious limitation to both clinical and basic neuroscience applications because stimulation of non-target brain regions may affect clinical outcomes, and certainly affect the degree to which any observed changes in behavior can be attributed to stimulation alone. A constant background fear by researchers or clinicians has been associated with understanding and controlling electric field depth and focality. This fear concerns an increased risk of accidental seizure and other adverse side effects.

The variety of types of magnetic fields which might be of interest in the study of magnetic brain stimulation has been described by Deng et al. In these studies a spherical saline-filled phantom was used to model the human head.

Additional relevant information may be found in "Three-dimensional distribution of the electric field induced in the brain by transcranial magnetic stimulation using Figure-8 and deep H-Coils," by Roth, Amir, Levkovitz, and Zangen in the Journal of Clinical Neurophysiology (2007 February; 24(1):31-8); "Coil Design Considerations for Deep-Brain Transcranial Magnetic Stimulation (dTMS)," by Deng, Peterchev, and Lisanby, 30th Annual International IEEE EMBS Conference, Vancouver, British Columbia, Canada, Aug. 20-24, 2008; and "Electric field depth-focality tradeoff in transcranial magnetic stimulation: Simulation comparison of 50 coil designs," in Brain Stimulation 6 (2013) 1-13 Brainsway, 19 Hartum Street, Bynet Building, 3rd floor, Har Hotzvim, Jerusalem 9777518, Israel.

The Brainsway reference provides a wide-ranging description of a whole family of coils called Hesed (H) coils that have been proposed to achieve effective stimulation of deep brain structures. The Hesed coils have complex winding patterns and larger dimensions compared to conventional TMS coils and consequently can be expected to have reduced electro-magnetic field depth attenuation and reduced focality. It has been proposed to use high-permeability ferromagnetic cores to improve the electric efficiency, field penetration, and focality of Hesed coils.

In short, there has long been interest in transcranial magnetic stimulation but as yet no effective way to produce controlled, predictable and safe stimulation deep inside the brain. A device that would achieve these goals would be advantageous in research and in medical treatment.

SUMMARY

This disclosure describes a method of creating more nearly parallel magnetic force field lines at a significant distance from the electro-magnetic apparatus that generates the magnetic field. The electro-magnetic apparatus has a quadrupole electro-magnet that may include a solenoid with or without a ferromagnetic core coaxial with the quadrupole. The quadrupole functions like a magnetic lens, and thus permits focusing of the magnetic force field lines. Such a construction, placed adjacent to the subject tissue creates field lines capable of deeper penetration.

The electro-magnetic apparatus comprises a quadrupole having two elongated C-shaped electro-magnets oriented so that the poles comprise a North-South-North-South sequence about a common axis perpendicular to the plane of the ends of the elongated C-shaped magnets. This arrangement will provide for increased depth of field penetration and improve focality in various brain stimulation models including TMS. One or more solenoidal electro-magnets may be mounted coaxially to the quadrupole electro-magnets' axis thereby providing a driving force for charged particles (for example, drug ions) and permitting deep penetration, not only of the magnetic field for TMS but also for introducing charged particles directly into the cerebrospinal fluid (CSF) surrounding the brain.

By using an electro-magnetic apparatus that includes at least one electro-magnetic quadrupole lens and at least one coaxially mounted solenoid, a unidirectional, focused, magnetic field can be established that may be used in two ways. First, it produces an electric stimulation in the brain believed to have therapeutic effect and useful for TMS experimental evaluations and clinical treatments. Second, it will both accelerate and focus a beam of charged particles by generating a force field parallel to the quadrupole axis. That focused beam drives the charged particles deep into biological tissue, including into tissue other than the brain, with minimal field divergence. The quadrupole design focuses a flow of charged particles while the solenoidal field accelerates the flow. The charged particles may include pharmaceuticals.

Solenoidal coils lead to more nearly parallel field lines that remain bunched together at greater distances from the plane perpendicular to the electro-magnetically coil axis. The combination of a solenoid and quadrupole electro-magnets biases the quadrupolar field by the solenoidal field in such a manner that charged particles may be transported along the common solenoidal-quadrupolar axis and concentrated in small, nearly spherical regions deep within biological tissues including, for example, the brain, kidneys, liver, and muscles.

The described electro-magnetic apparatus is mounted to an articulating arm that allows it to be rotated in both the sagittal and coronal planes and in planes parallel to the sagittal and coronal planes. The focused beam from the electro-magnetic apparatus may be used to for treatment of neurological and psychiatric disorders and delivery of pharmaceuticals to the target area.

A feature of the invention is an elongated, C-shaped, electro-magnet having non-parallel pole piece faces coupled with a similar, opposing, inverted, and elongated C-shaped electro-magnet so that the north and south poles of the two electro-magnets alternate at regularly spaced intervals, thereby creating a symmetrical quadrupolar magnetic field. Pole pieces in the preferred quadrupole arrangement are oriented at 45° with respect to the proposed elongated C-shaped electro-magnets.

To drive this electro-magnetic apparatus for tissue penetration, pulses of direct current must be generated. A power supply for generating the pulses may require energy storage and one or more phase-adjusting capacitors. Pulses less than 10 microseconds are suitable for brain stimulation and can produce magnetic fields of several Teslas.

Another feature of the disclosure is extending of the pole pieces parallel to the electro-magnetically quadrupole axis, so that this elongated electro-magnetic assembly may be as much as approximately ten times the length of the internal portion of the axis of the electro-magnet, resulting in an aspect ratio several times (2-10×) that of a standard C-shaped electro-magnet.

Another feature of the disclosure is that the solenoid may have a ferromagnetic core, mounted coaxially with the quadrupole's focal axis.

Yet another feature of the disclosure is a solenoidal coil that has an axis coaxial with the quadrupole's focal axis and is inserted within the C-shaped quadrupole electro-magnets, and is either wholly contained within the quadrupole or extends from one or both of the quadrupole's ends beyond the planes defined by the ends of the quadrupole.

A feature of the disclosure is the mounting of the electro-magnetic apparatus to an articulating arm so that it can be rotated in either the sagittal and coronal planes about a point located on the intersection of those planes or any two planes parallel to the sagittal and coronal planes. The sagittal plane is the vertical plane passing through the top of the head and dividing the nose. The coronal plane passes vertically through the top of the head and the ears. The sagittal plane and the coronal plane are perpendicular to each other with the intersection being the line passing vertically through the center of the top of the head.

Another feature of the disclosure is the use of a stacked array of multiple quadrupoles having poles oriented at 90° with respect to the adjacent quadrupole in order to achieve improved focality, and use of this stacked array combined with solenoids to achieve a focused beam capable of deeper penetration while creating a driving field for charged particles. The number of quadrupoles in the array is preferably an even number greater than four.

Those skilled in the art of transcranial magnetic stimulation will appreciate many other features and their advantages from a careful reading of the detailed description, accompanied by the drawings.

BRIEF DESCRIPTION OF THE DRAWINGS

In the drawings,

FIG. 1 is a left rear perspective view of the present electro-magnetic beam generator, according to an aspect of the disclosure;

FIG. 2 is a left front perspective view of the present electro-magnetic beam generator, according to an aspect of the disclosure;

FIG. 5 is a front view of the present electro-magnetic beam generator, according to an aspect of the disclosure;

FIG. 6 is a bottom view of the present electro-magnetic beam generator, according to an aspect of the disclosure;

FIG. 7 is a top view of the present electro-magnetic beam generator, according to an aspect of the disclosure;

FIG. 8 is a rear view of the present electro-magnetic beam generator, according to an aspect of the disclosure;

DETAILED DESCRIPTION

Figure 3:
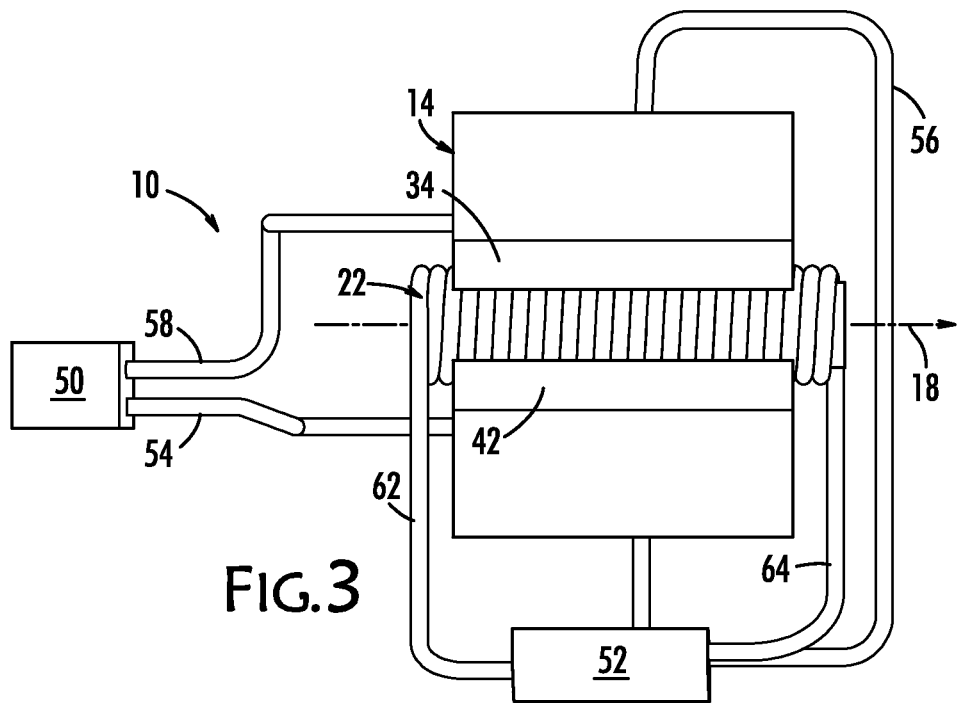
FIG. 3 is a right side view of the present electro-magnetic beam generator, according to an aspect of the disclosure.
Figure 4:
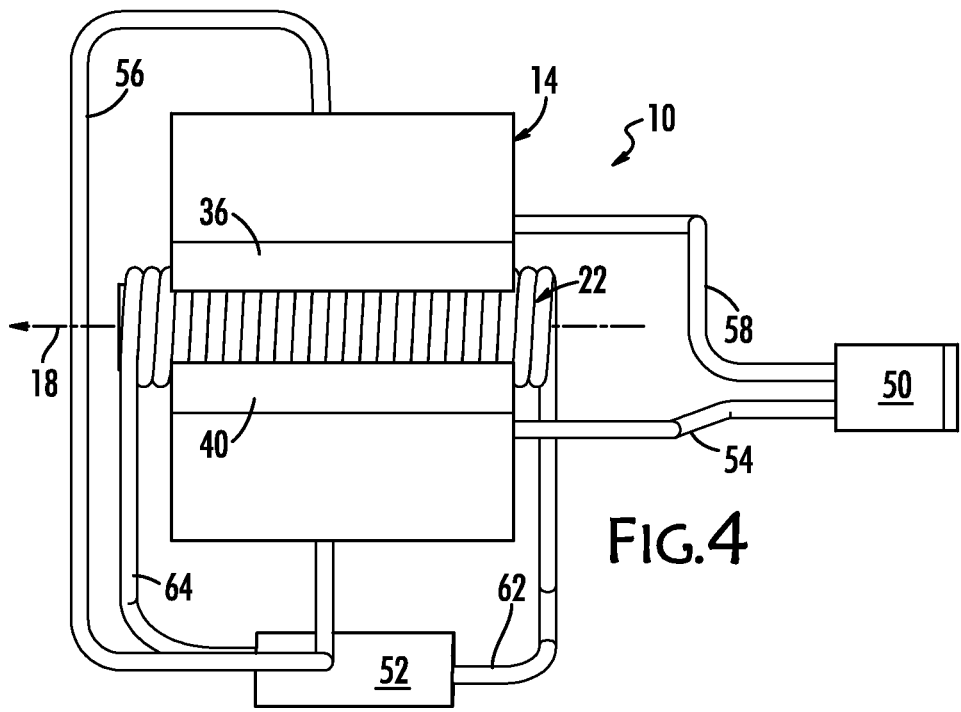
FIG. 4 is a left side view of the present electro-magnetic beam generator, according to an aspect of the disclosure.

Referring now to FIGS. 1-8, there is shown an electro-magnetic apparatus 10 suitable for transcranial stimulation and other purposes. Apparatus 10 includes a quadrupole 14 having a common axis 18 with a solenoid 22.

Quadrupole 14 is constructed of two elongated C-shaped electro-magnets 26, 28, each having a coil 30, 32. Electro-magnet 26 has non-parallel pole pieces 34, 36, and electro-magnet 30 has non-parallel pole pieces 40, 42. Pole pieces 34, 36, 40, 42, represent magnetic North, South, North, South, respectively.

Electro-magnet 26 is inverted with respect to electro-magnet 28 so that North-South poles alternate at regularly spaced intervals, thereby creating a symmetrical quadrupole field. Additionally, pole pieces 34, 36, 40, 42, in the preferred quadrupole arrangement are at 45° to their respective elongated C-shaped electro-magnets 26, 28, as best seen in FIG. 5.

A driving power supply 50 for quadrupole 14 and a power supply 52 for solenoid 22 may require energy storage plus one or more additional phase-adjusting capacitors in order to apply pulsed direct current. Current is carried from power supply 50 to and from coils 30, 32, via conductors 54, 56, and 58, and to power supply 52 via conductors 62, 64.

Pole pieces 34, 36, 40, 42, may extend in a direction parallel to common axis 18 by as much as approximately 10 times the length of coils 30, 32. The elongation of electro-magnetic apparatus 10 may create an aspect ratio several times (2-10×) that of a standard C-shaped electro-magnet.

For example, pole pieces 34, 36, 40, 42 may be made of a ferromagnetic material 1-3 mm thick. Pole pieces 34, 36, 40, 43 may be made by bending, or otherwise shaping, and then annealing steel plate to obtain the 45 degree angle, being careful to obtain uniformity at the Neel boundaries in the immediate vicinity of the bend. Alternatively, a 3-dimensional printer may be used to form a model of a pole piece and the core as a single unit. A sand mold may be made from the model, filled with ferromagnetic material, and sintered. Other manufacturing methods known to those skilled in the art may alternatively be used.

Solenoid 22 may also extend beyond one or both of the planes defined by the ends of the pole pieces 34, 36, 40, 42. Solenoid 22 may have a core 70, as shown, which may be hollow and may be made of a ferromagnetic material or may be made of a non-ferromagnetic material. Core 70 provides support for the coils of solenoid 22.

Common axis 18 is the focal axis of quadrupole 14 and the axis of solenoid 22 and is therefore the axis of electro-magnetic device 10. Having common axis 18 for both quadrupole 14 and solenoid 22 creates a magnetic field bias which can be used to drive charged particles along common axis 18 into the subject tissue.

Figure 9:
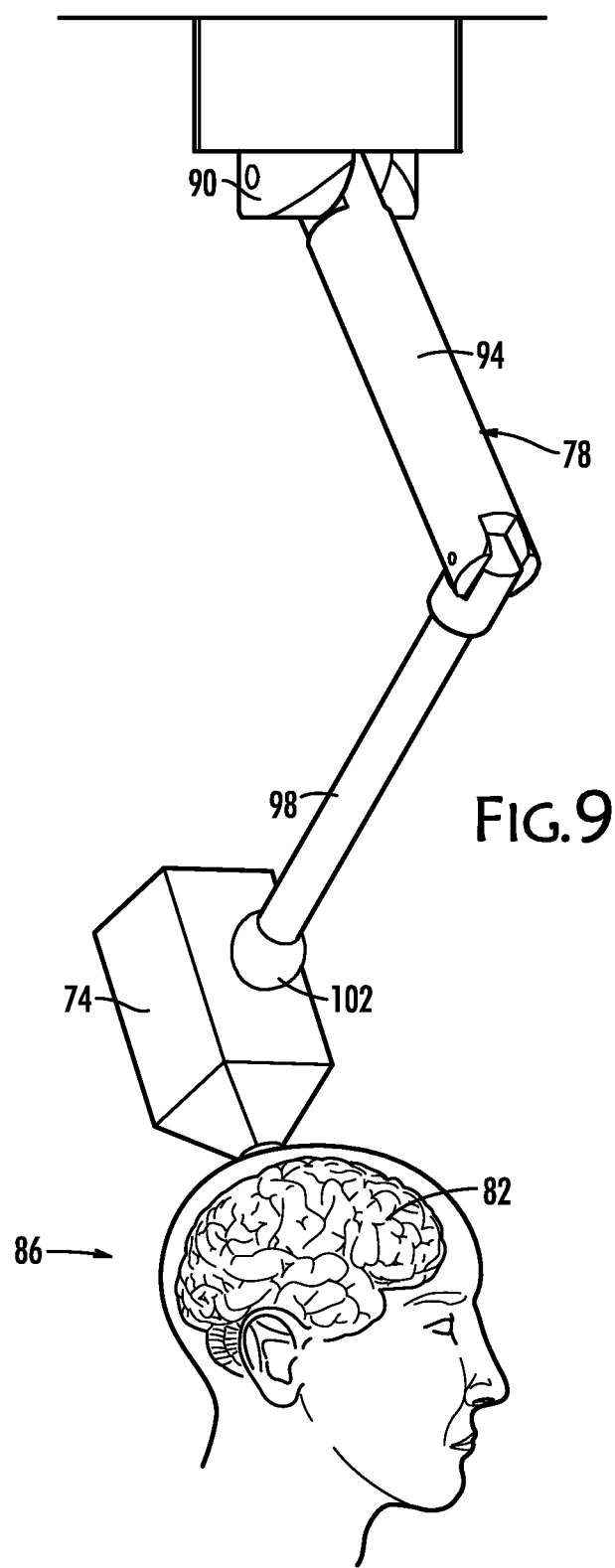
FIG. 9 is a perspective view of the present electro-magnetic beam generator suspended from a positioning arm, according to an aspect of the disclosure—Sagittal and Coronal Planes for Human Head.

Referring now to FIG. 9, there is illustrated the present electro-magnetic apparatus in a housing 74 suspended from an articulated arm 78 so as to be placed in position to stimulate the brain 82 of a patient 86. Articulating arm 78 has a swivel base 90, a pivotable first section 94, and a pivotable second section 98 and a rotatable end effector 102, all of which provide for positioning and orienting of housing 74 so that the common axis 22 of electro-magnetic apparatus 10, as illustrated in FIGS. 1-8, can be pointed at and brought close to any part of brain 82 of patient 86. In particular, articulating arm 78 must be capable of positioning housing 74 so that electro-magnetic apparatus 10 can be rotated in both the sagittal and coronal planes about a point located on the intersection of those planes as well as any and all planes parallel to these two planes so that a region of interest anywhere in brain 82 of patient 86 may be exposed to the magnetic field generated. The sagittal plane is the vertical plane passing through the top of the head and the nose. The coronal plane is the vertical plane that passes through the top of the head and the ears. The sagittal plane and the coronal plane are perpendicular to each other with the intersection being the line passing vertically through the top of the head.

In addition to brain stimulation, quadrupole 14 comprises two extended C-shaped electro-magnets 26, 30, with or without solenoid 22, which is able to drive a focused charged particle beam into the subject tissue (brain, muscle, bone, liver, kidney, etc.). When used to deliver charged particles to tissues other than brain tissues, the same articulating arm 78 may be used to position housing 74 with respect to the tissue of patient 86 to which the charged particles are to be delivered.

For delivering charged particles, a stacked array of quadrupoles 14 aligned along a common axis 18 with a longer solenoid 22 may be used to further improve focality at greater depth. Also, in addition to using several quadrupoles, the number of poles may be increased beyond the four poles in quadrupole 14 to six, eight or a higher (even) number of poles.

The length of the longer solenoid could be co-terminus with the length of the stacked quadrupoles or might extend beyond the ends of the stacked quadrupole ends, or be limited within the plane of the quadrupole ends. Adjacent electro-magnetic apparatuses 10, as illustrated in FIGS. 1-8, can be placed coaxially, their ends separated by a short distance—between 0.1-1.0 times the apparatus length—from one another and each quadrupole oriented so that its poles are at 90° with respect to the next quadrupole assembly.

Those skilled in the art of transcranial magnetic stimulation apparatus design will appreciate that many modifications and substitutions may be made to the aspects of the disclosure presented above without departing from the spirit and scope of the appended claims.

What is claimed is:

1. Apparatus, comprising:
    a magnetic quadrupole with pole pieces arranged in opposing pairs of pole pieces and with an axis perpendicular to the planes defined by the ends of said pole pieces; and
    a solenoid having an axis, said axis of said solenoid being co-axial with said axis of said magnetic quadrupole.

2. The apparatus of claim 1, wherein said solenoid is positioned between said opposing pairs of pole pieces.

3. The apparatus of claim 1, further comprising at least one power supply for energizing said magnetic quadrupole and said solenoid.

4. The apparatus of claim 3, wherein said at least one power supply is configured to generate current pulses.

5. The apparatus of claim 4, wherein said current pulses are less than 10 micro-seconds in duration.

6. The apparatus of claim 3, wherein said at least one power supply is two power supplies, a first power supply generating a first current pulse in said magnetic quadrupole and a second power supply generating a second current pulse in said solenoid.

7. The apparatus of claim 6, wherein said first and second current pulses are generated simultaneously.

8. The apparatus of claim 7, wherein said first and second current pulses are less than 10 microseconds in duration.

9. The apparatus of claim 3, wherein said solenoid extends axially beyond the ends of said pole pieces.

10. The apparatus of claim 1, wherein said solenoid further comprises a core.

11. The apparatus of claim 10, wherein said core is made of ferromagnetic material.

12. The apparatus of claim 10, wherein said core is hollow.

13. A method for using the apparatus of claim 1, comprising the steps of:
    a. directing said apparatus at human tissue; and
    b. generating current pulses in said magnetic quadrupole and said solenoid.

14. The method of claim 13, wherein said tissue is brain tissue.

15. The method of claim 13, wherein said current pulses is a series of current pulses.

16. The method of claim 13, further comprising the steps of:
    a. ionizing a pharmaceutical agent; and
    b. injecting said pharmaceutical agent into cerebrospinal fluid surrounding the brain and at the point where the axis of the solenoid enters the tissue said solenoid when said current pulses are generated.

17. An apparatus, comprising:
at least one magnetic quadrupole, a quadrupole of said at least one quadrupole having pole pieces arranged in opposing pairs of pole pieces and with an axis perpendicular to the planes defined by the ends of said pole pieces; and
a solenoid having an axis, said axis of said solenoid being co-axial with said axis of said at least one magnetic quadrupole, said solenoid is positioned between said opposing pairs of pole pieces.

18. The apparatus of claim 1, wherein said at least one magnetic quadrupole is two magnetic quadrupoles, and wherein pole pieces of a first quadrupole of said at least two quadrupoles alternate north and south with pole pieces of a second quadrupole of said two quadrupoles.

19. The apparatus of claim 18, wherein said second quadrupole and said first quadrupole are axially separated by a distance no greater than the length of said first quadrupole.

20. The apparatus of claim 18, wherein said solenoid extends axially beyond the ends of said at least one quadrupole.

\* \* \* \* \*